(12) United States Patent
Todokoro et al.

(10) Patent No.: US 6,216,692 B1
(45) Date of Patent: Apr. 17, 2001

(54) AIRWAY ADAPTOR FOR MEASUREMENT OF GAS CONCENTRATION

(75) Inventors: Noriaki Todokoro; Hidetoshi Dainobu; Shinji Yamamori, all of Tokyo (JP)

(73) Assignee: Nihon Kohden Corporation, Tokyo (JP)

( * ) Notice: Subject to any disclaimer, the term of this patent is extended or adjusted under 35 U.S.C. 154(b) by 0 days.

(21) Appl. No.: 09/334,564

(22) Filed: Jun. 21, 1999

(30) Foreign Application Priority Data

Jun. 19, 1998 (JP) .................................. 10-172455

(51) Int. Cl.[7] ...................................... A62B 7/00
(52) U.S. Cl. .................. 128/205.23; 128/204.23
(58) Field of Search ................ 128/204.23, 205.12, 128/205.23; 600/532

(56) References Cited

U.S. PATENT DOCUMENTS

| | | | |
|---|---|---|---|
| 4,177,381 | * 12/1979 | Mcclatchie et al. | 250/343 |
| 4,678,488 | * 7/1987 | Howard et al. | 128/205.12 |
| 4,886,528 | * 12/1989 | Aaltonen et al. | 600/532 |
| 4,914,720 | * 4/1990 | Knodle et al. | 600/532 |
| 5,067,492 | * 11/1991 | Yelderman et al. | 600/532 |
| 5,095,900 | * 3/1992 | Fertig et al. | 600/532 |
| 5,159,934 | * 11/1992 | Hoberman | 600/532 |
| 5,261,415 | * 11/1993 | Dussault | 600/532 |
| 5,282,473 | * 2/1994 | Braig et al. | 600/532 |
| 5,925,831 | * 7/1999 | Storsved | 128/204.23 |
| 5,932,877 | * 8/1999 | Braig et al. | 600/532 |
| 5,957,127 | * 9/1999 | Yamamori et al. | 600/532 |

* cited by examiner

Primary Examiner—Aaron J. Lewis
(74) Attorney, Agent, or Firm—Sughrue, Mion, Zinn Macpeak & Seas, PLLC

(57) ABSTRACT

Windows 2 which allow infrared light to be transmitted therethrough are opened at opposed positions of side walls of a flow tube 1, respectively. A hexagonal frame 6 is air tightly attached to each of the apertures. Each frame 6 is protruded from the inner face of the flow tube 1. A transparent window on which an anti-fogging layer 5 is formed stretches on the inner face of each of the frame 6, so that waterdrops flowing through the flow tube 1 are caused to flow along both the sides of the frame 6, thereby preventing the waterdrops from flowing over the anti-fogging layer 5.

13 Claims, 4 Drawing Sheets

AIRWAY ADAPTOR FOR MEASUREMENT OF GAS CONCENTRATION

BACKGROUND OF INVENTION

1. Field of Invention

The present invention relates to an airway adaptor for measurement of the concentration of carbon dioxide gas. Such an airway adaptor is attached to a respirator in order to measure the concentration of carbon dioxide gas in a respiratory gas.

2. Related Art

When respiration of a patient is artificially performed by using a respirator, an airway adaptor is attached to a flow path of the respirator, so as to measure the concentration of carbon dioxide gas in a respiratory gas. FIG. 4 is an external perspective view showing the configuration of an example of an airway adaptor of the prior art. Referring to FIG. 4, a center portion in the axial direction of a cylindrical flow tube 1 has a tubular shape having a rectangular section. Circular apertures 2 which allow infrared light to be transmitted therethrough are opened at opposed positions of side walls of the portion, respectively.

As shown in a section view of FIG. 5, a step portion 3 in which the inner side has a smaller diameter is concentrically formed in the inner periphery of each of the apertures 2. A transparent window 4 serving as a transparent film which is made of polyester or the like and formed into a disk-like shape is applied to the window via the step portion 3. An anti-fogging layer 5 is applied to or deposited on the inner face of the transparent window 4.

FIG. 6 is a section view showing the configuration of another example of a prior art method of fixing the transparent window 4 to the aperture 2, and corresponding to FIG. 5. Referring to FIG. 6, the outer periphery of the transparent window 4 is fixed to or heat-found on the inner periphery of the aperture 2 by the frame 6 with caulking the frame from the outside. In this case, the anti-fogging layer 5 on the inner surface of the transparent sheet 4 is substantially flush with the inner wall face of the flow tube 1.

In the prior art example shown in FIG. 5, the step is formed between inner wall of the flow tube 1 and the inner-surface of the anti-fogging layer 5, and hence the moisture content in a respiratory gas is condensed into waterdrops thereon. As shown in FIG. 7, the condensed waterdrop 7 gathers in the gravitational direction of the step portion. Therefore, the amount of infrared light which is transmitted through the window 2 is reduced, thereby producing a measurement error.

In the prior art example shown in FIG. 6, since the inner wall of the flow tube 1 is substantially flush with the inner face of the anti-fogging layer 5, there is no fear that water gathers around the inner periphery of the aperture 2 because there is no step portion as with the prior art example of FIGS. 5 and 7. When the airway adaptor is positioned such that transparent window 4 is arranged horizontally water condensed in a flow tube flows along the inner wall of the flow tube 1, however, water passes over the anti-fogging layer 5 as shown in FIG. 8, and hence there arises a fear that a measurement error may occur.

SUMMARY OF INVENTION

The invention has been conducted in view of the foregoing circumstances. It is an object of the invention to provide an airway adaptor for measuring the concentration of carbon dioxide gas which prevents waterdrops in a flow tube from passing over an inner surface of the transparent window, on measurement, thereby allowing measurement to be stably performed for a long term.

In order to attain the object, the invention is an airway adaptor for measurement of a gas concentration comprising:

a flow tube through which a respiratory gas flows;

transparent windows formed at opposed positions of side walls of said flow tube, and allowing infrared light to be transmitted therethrough; and a water path formed on said side wall to prevent a waterdrop from being passed over said transparent windows.

According to this configuration, when waterdrops due to the moisture content in a respiratory gas flowing through the flow tube flows along the inner wall of the flow tube, the waterdrops pass over the water path formed in the frame, which do not pass over the transparent films on windows. Therefore, the waterdrops are prevented from passing over the transparent films which stretch on the inner faces of the frames. As a result, infrared light transmitted through the transparent films is not interrupted by the waterdrops, and hence a measurement error does not occur.

The water path is formed by projecting the frame from the inner surface of the flow tube. The frame is sealingly fitted on an inner peripheral portion of the aperture and stretches the transparent sheets on the inner faces thereof. As a result, the waterdrop passes through the outer peripheral portion of the frame.

On the other hand, when the frame is formed beyond a narrowed portion of the flow tube, the flow path is formed in a space before the narrowed portion so that the device is more free from the phenomenon that waterdrops pass over the transparent sheets.

Further, when the taper portion is provided on the narrowed portion of the flow tube, waterdrop splashing by hitting against an entrance portion is avoided of the narrowed portion.

DETAILED DESCRIPTION OF PREFERRED EMBODIMENTS

Figure 1:
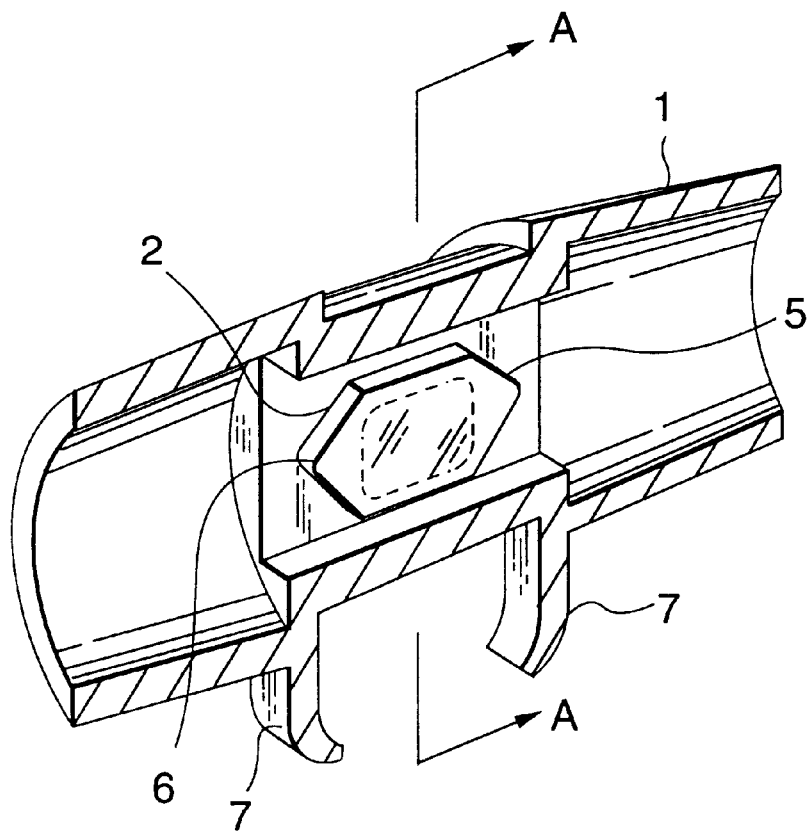
FIG. 1 is a section view showing the configuration of an embodiment of the airway adaptor for measurement of the gas concentration of the present invention, and taken along the axis.
Figure 2:
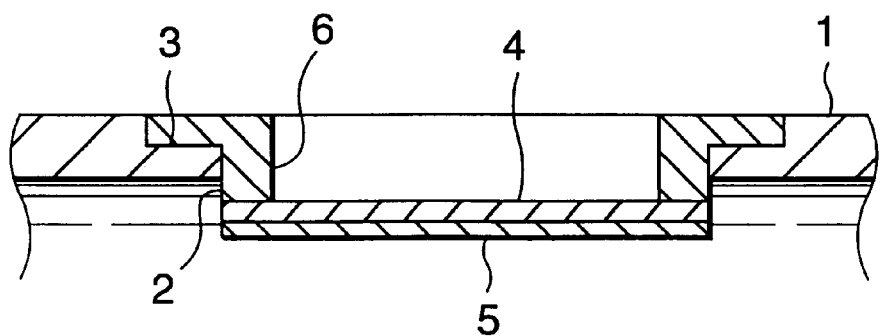
FIG. 2 is a section view taken along the line A—A.
Figure 4:
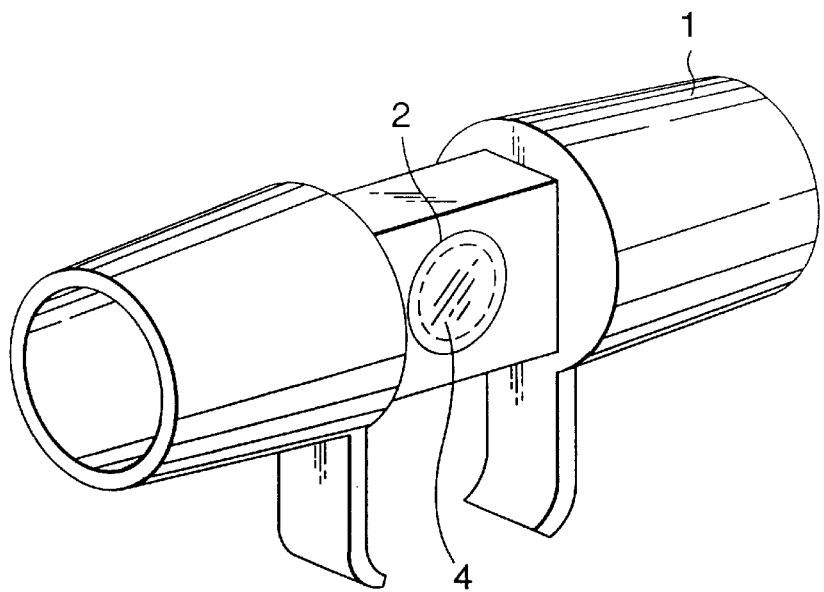
FIG. 4 is an external perspective view showing the configuration of an example of a prior art airway adaptor for measurement of the gas concentration.
Figure 5:
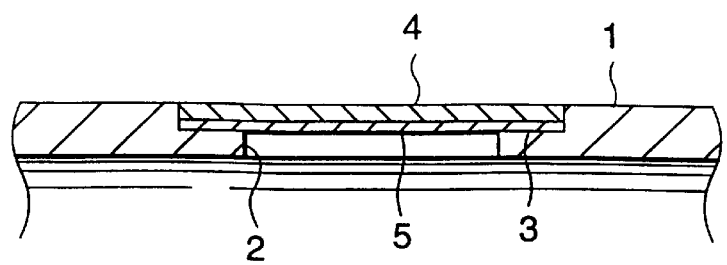
FIG. 5 is a section view showing a first example of a structure for attaching a transparent sheet to a flow tube in the prior art.
Figure 6:
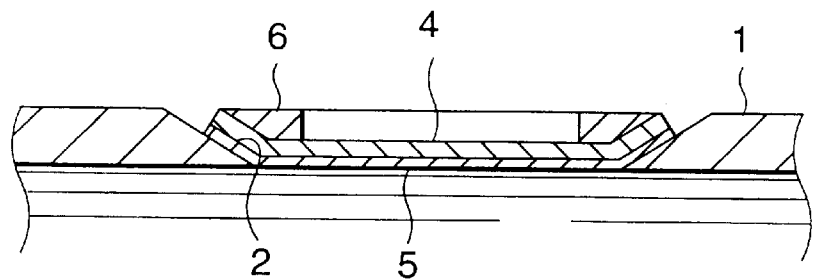
FIG. 6 is a section view showing a second example of a structure for attaching a transparent sheet to a flow tube in the prior art.
Figure 7:
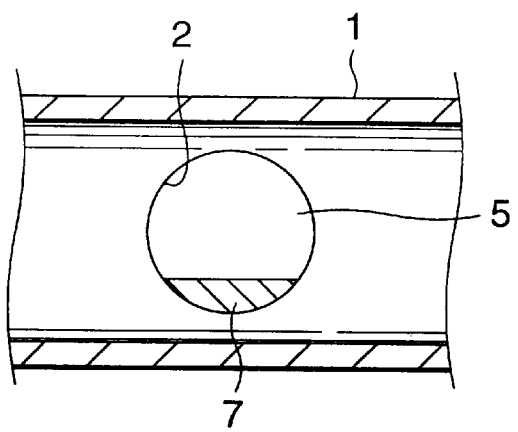
FIG. 7 is a diagram showing waterdrops collecting in the first embodiment shown in FIG. 5.
Figure 8:
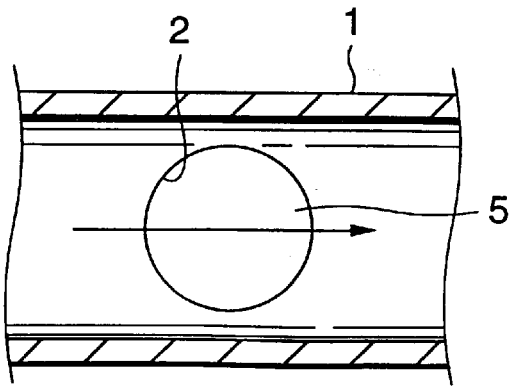
FIG. 8 is a diagram showing a waterdrops flowing without collecting in the second embodiment shown in FIG. 6.

Hereinafter, the configuration of an embodiment of the airway adaptor for measuring the concentration of carbon dioxide gas according to the invention will be described with reference to the accompanying drawings. FIG. 1 is a section view showing the configuration of one embodiment of the invention, and taken along the axis, and FIG. 2 is a section view showing the structure for attaching the transparent sheet 4 of FIG. 1 and taken along the line A—A. In the figures, portions corresponding to those of the prior art examples shown in FIGS. 4, 5, and 6 are designated by the same reference numerals, and their description is omitted.

Referring to FIGS. 1 and 2, frame 6 serving as the frames are formed into a hexagonal shape. The frame 6 are fitted into the apertures 2 which are formed at opposed positions of the side walls of the flow tube 1, respectively, while a flange of each frame abuts against the step portion 3 of the corresponding aperture 2, so as to be air tightly fixed to the aperture. The portion of the inner side of each of the frame 6 is inwardly protruded from the inner peripheral face of the flow tube 1. The transparent sheet 4 has an inner surface of which an anti-fogging layer 5 is formed, and said transparent sheet 4 is fixed to an end surface of the frame 6 which is inwardly protruded into the flow tube 1. The reference numeral 7 denotes an attachment portion for fixing a unit having an infrared light emitting unit and a light receiving unit which are not shown, to the flow tube 1.

Figure 3:
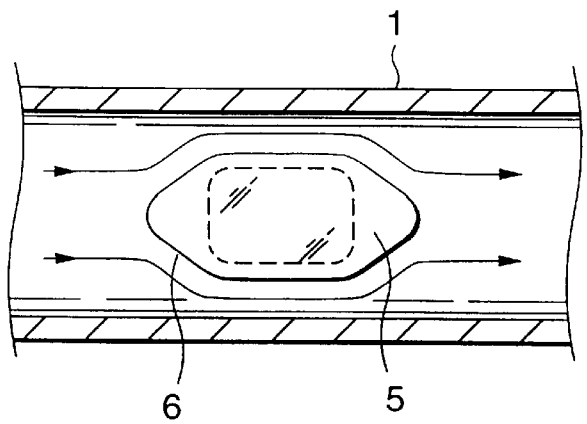
FIG. 3 is a view showing a flow of waterdrops in a flow tube of FIG. 1.

According to the embodiment, when the airway adaptor is attached to a flow path of a respirator, waterdrops due to the moisture content in a respiratory gas flowing through the flow tube 1 flows along the inner wall of the flow tube 1. At this time, as shown in FIG. 3, the waterdrops pass over the outer side of each frame 6, as the water path, which frame 6 are protruded from the inner face of the flow tube 1. Therefore, the waterdrops are prevented from passing over the anti-fogging layers 5 of the transparent sheets 4 which stretch on the inner faces of the frame 6. As a result, infrared light transmitted through the transparent sheets 4 is not interrupted by the waterdrops, and hence an error does not occur in measurement of the concentration of carbon dioxide gas in a respiratory gas.

Figure 9:
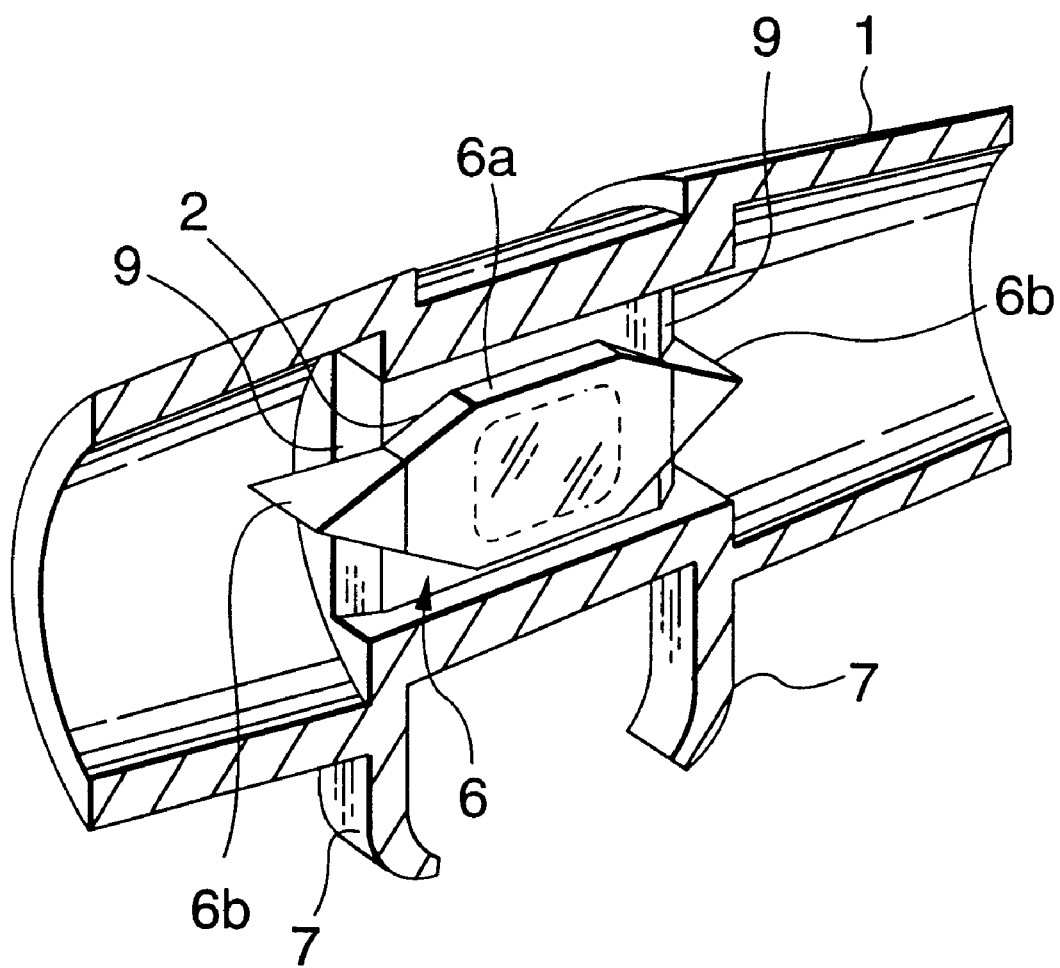
FIG. 9 is a section view showing the configuration of another embodiment of the airway adaptor of the present invention.

On the other hand, as shown in FIG. 9, it is applicable for forming the frame 6 to an area positioned beyond a narrowed portion of the flow tube 1. In this circumstance, the frame 6 is constituted of the body portion 6a and a pair of end portions 6b, and is formed into a hexagonal shape. The body portion is slightly different from the embodiment described above. However, the substantive structure is the same as the embodiment described above. Namely, the body portion 6a is sealingly fitted on the aperture portion in such a manner that the flange portion of the body portion abuts against the flange portion of the stepped portion 3 of the aperture 2 (as shown in FIG. 2).

Each end portion 6b is uniformly formed with the flow tube at the inner portion thereof. The tip end of the end portion 6b extends until a space without the narrowed portion. As a result, before entering the narrowed portion of the flow tube, the flow path is divided by the frame 6 so that the device is more free from the phenomenon that the waterdrop passes over the transparent sheets.

As shown in FIG. 9, the taper portion is formed at an inner apex portion of the flow tube on a narrowed portion 9, that is, the enter portion is defined at the entrance portion of the narrowed portion 9. As a result, splashing the waterdrop by hitting against an entrance portion of the narrowed portion 9 is avoided thus and more effectively preventing the waterdrops from passing over the transparent film.

In the embodiment described above, the frame 6 is formed into a hexagonal shape. The shape of the frame 6 is not restricted to a hexagon. The frame may have any other shape as far as the shape produces a small flow resistance against a respiratory gas flowing through the flow tube 1. Sapphire may be applied as transparent windows, as long as a frame is formed.

As described above, according to the airway adaptor for measuring the gas concentration of the invention, apertures which allow infrared light to be transmitted therethrough are opened at opposed positions of side walls of a flow tube, respectively, and have a flow path for preventing the waterdrop from being passed over the transparent film. Therefore, waterdrops due to the moisture content in a respiratory gas flowing through the flow tube pass over the outer side of each of the frames which are protruded from the inner face of the flow tube, so that the waterdrops are prevented from passing over the transparent films which stretch on the inner faces of the frames.

As a result, infrared light transmitted through the transparent films is not interrupted by the waterdrops. Consequently, an error does not occur in measurement of the concentration of carbon dioxide gas, thereby allowing measurement to be stably performed for a long term.

What is claimed is:

1. An airway adaptor for measurement of a gas concentration comprising:
    a flow tube through which a respiratory gas flows;
    transparent windows formed at opposed positions of side walls of said flow tube, and allowing infrared light to be transmitted therethrough; and
    a water path formed on said side walls for diverting waterdrops around said transparent windows.

2. The airway adaptor as claimed in claim 1, wherein said water path is formed by a frame protruded from an inner surface of said side wall.

3. The airway adaptor as claimed in claim 2, wherein said transparent windows are positioned at inner surfaces of said protruded frame, respectively.

4. The airway adaptor as claimed in claim 2, wherein said frame includes portions formed beyond a narrowed portion of said flow tube.

5. The airway adaptor as claimed in claim 1, wherein a taper portion formed on said side walls of a narrowed portion of said flow tube diverts said waterdrops.

6. The airway adaptor as claimed in claim 1, wherein an anti-fogging layer is formed on inner surfaces of said transparent windows.

7. A flow tube adapter for measuring a concentration of respiratory gases in a respiratory flow tube, said flow tube adapter comprising:
    a body portion;
    apertures formed in said body portion, wherein each aperture is positioned on opposing walls of said body portion;
    windows made of transparent material disposed in said body portion to cover said apertures; and
    liquid path diversion sections disposed along an inner wall of said body portion for diverting liquid present in said body portion around said windows.

8. The flow tube adapter according to claim 7, wherein said liquid path diversion sections each comprise a frame protruding from said inner wall of said body portion around said apertures, wherein said windows are mounted on respective frames.

9. The flow tube adapter according to claim 8, further comprising an anti-fog material disposed over said windows.

10. The flow tube adapter according to claim 8, wherein a section of said body portion having opposing apertures has a narrowed cross section with respect to sections of the body portion without said apertures, and wherein said frame being substantially located on the inner wall of said narrowed cross section has tapered ends thereof extending beyond the narrowed cross section along axial directions of said body portion.

11. The flow tube adapter according to claim 8, further comprising an attachment portion for fixing an infrared detection unit to said flow tube adapter.

12. The flow tube adapter according to claim 7, further comprising an attachment portion for fixing an infrared detection unit to said flow tube adapter.

13. A respirator having flow tube adapter for measuring a concentration of respiratory gases in a respiratory flow tube, said flow tube adapter comprising:

a body portion;

apertures formed in said body portion, wherein each aperture is positioned on opposing walls of said body portion;

windows made of transparent material disposed in said body portion to cover said apertures; and liquid path diversion sections disposed along an inner wall of said body portion for diverting liquid present in said body portion around said windows.

* * * * *